United States Patent [19]

Hubele

[11] Patent Number: 4,897,396
[45] Date of Patent: Jan. 30, 1990

[54] 2-PHENYLAMINO PYRIMIDINE DERIVATIVES AND THEIR USES AS MICROBICIDES

[75] Inventor: Adolf Hubele, Magden, Switzerland

[73] Assignee: Ciba-Geigy Corporation, Ardsley, N.Y.

[21] Appl. No.: 202,770

[22] Filed: Jun. 3, 1988

[51] Int. Cl.$^4$ ............................................. C07D 239/02
[52] U.S. Cl. ..................................... 514/275; 544/332
[58] Field of Search ......................... 544/332; 514/275

[30] Foreign Application Priority Data

Jun. 11, 1987 [CH] Switzerland .......................... 2188/87
Apr. 11, 1988 [CH] Switzerland .......................... 1318/88

[56] References Cited

U.S. PATENT DOCUMENTS

| 4,659,363 | 4/1987 | Hubele et al. | 71/92 |
| 4,694,009 | 9/1987 | Hubele et al. | 514/269 |
| 4,802,909 | 2/1989 | Rempfler et al. | 71/92 |
| 4,814,338 | 3/1989 | Ito et al. | 514/275 |

FOREIGN PATENT DOCUMENTS

| 0224339 | 6/1987 | European Pat. Off. | 544/332 |
| 151404 | 10/1981 | Fed. Rep. of Germany | 544/332 |
| 56-65804 | 6/1981 | Japan | 544/332 |
| 1245085 | 9/1971 | United Kingdom | 544/332 |

OTHER PUBLICATIONS

Chem. Abstr., 103: 6301.r (1985).
Patent Abstracts of Japan, 11, 317 (1987), Abstract of JP-62/106084.

Primary Examiner—Mary C. Lee
Assistant Examiner—J. Richter
Attorney, Agent, or Firm—Edward McC. Roberts

[57] ABSTRACT

Novel compounds of the formula

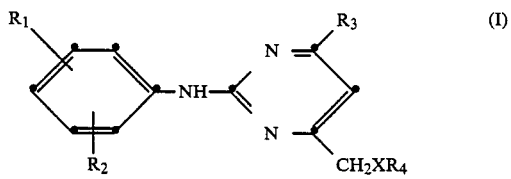

in which:

$R_1$ and $R_2$ independently of one another are hydrogen, halogen, $C_1$–$C_3$-alkyl, $C_1$–$C_2$-haloalkyl, $C_1$–$C_3$-alkoxy or $C_1$–$C_3$-haloalkoxy;

$R_3$ is hydrogen; $C_1$–$C_4$-alkyl; $C_1$–$C_2$-alkyl substituted by halogen or by hydroxy; cyclopropyl; or cyclopropyl substituted by halogen and/or by methyl;

$R_4$ is $C_1$–$C_8$-alkyl; $C_2$–$C_6$-alkyl substituted by halogen, hydroxy, cyano, $C_1$–$C_4$-alkoxy, $C_3$–$C_4$-alkoxyalkoxy or by $C_1$–$C_3$-alkylthio; $C_3$–$C_6$-alkenyl; $C_3$–$C_6$-alkynyl; $C_3$–$C_7$-cycloalkyl; or $C_3$–$C_7$-cycloalkyl substituted by methyl; and X is oxygen or sulphur.

Compounds of formula I are valuable preparations for controlling microorganisms, especially in the agrochemical sector, and insect pests.

20 Claims, No Drawings

2-PHENYLAMINO PYRIMIDINE DERIVATIVES AND THEIR USES AS MICROBICIDES

The present invention relates to novel 2-anilinopyrimidine derivatives of formula I below. It relates also to the preparation of these substances and to agrochemical compositions that contain as active ingredient at least one of these compounds. The invention relates also to the preparation of the mentioned compositions and to the use of the active ingredients or of the compositions for controlling pests, especially harmful insects and plant-destructive microorganisms, preferably fungi.

The compounds according to the invention correspond to the general formula I

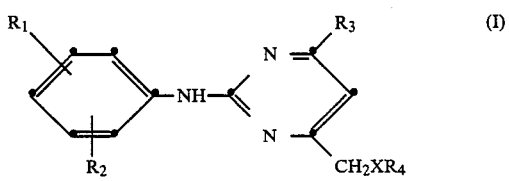

in which:

$R_1$ and $R_2$ independently of one another are hydrogen, halogen, $C_1$–$C_3$-alkyl, $C_1$–$C_2$-haloalkyl, $C_1$–$C_3$-alkoxy or $C_1$–$C_3$-haloalkoxy;

$R_3$ is hydrogen; $C_1$–$C_2$-alkyl; $C_1$–$C_2$-alkyl substituted by halogen or by hydroxy; cyclopropyl; or cyclopropyl substituted by halogen and/or by methyl;

$R_4$ is $C_1$–$C_8$-alkyl; $C_2$–$C_6$-alkyl substituted by halogen, hydroxy, cyano, $C_1$–$C_4$-alkoxy, $C_3$–$C_4$-alkoxyalkoxy or by $C_1$–$C_3$-alkylthio; $C_3$–$C_6$-alkenyl; $C_3$–$C_6$-alkynyl; $C_3$–$C_7$-cycloalkyl; or $C_3$–$C_7$-cycloalkyl substituted by methyl; and X is oxygen or sulphur.

Depending on the number of carbon atoms indicated, alkyl by itself or as a component of another substituent, such as haloalkyl or haloalkoxy, is to be understood as meaning, for example: methyl, ethyl, propyl, butyl, pentyl, hexyl, heptyl and octyl and their isomers, such as for example, isopropyl, isobutyl, tert.-butyl, isopentyl etc.. Halogen is fluorine, chlorine, bromine or iodine. Haloalkyl and haloalkoxy are mono- to per-halogenated radicals, such as, for example, $CHCl_2$, $CH_2F$, $CCl_3$, $CH_2Cl$, $CHF_2$, $CH_2CH_2Br$, $C_2Cl_5$, $CHBr$, $CHBrCl$, etc., preferably $CF_3$. Alkenyl is, for example, propen-1-yl, allyl, buten-1-yl, buten-2-yl or buten-3-yl, and also chains having several double bonds. Alkynyl is, for example, propyl-2-yl, butyn-1-yl, butyn-2-yl, pentyn-4-yl etc. preferably propargyl. Depending on the number of carbon atoms indicated, cycloalkyl is, for example, cyclopropyl, cyclobutyl, cyclopentyl, cyclohexyl or cycloheptyl.

Compounds having an N-pyrimidylaniline structure are already known. For example, in published Japanese patent application Sho 56-65804 and in GDR patent specification No. 151404, compounds that have this basic structure are described as being effective against plant pests. However, the known compounds have hitherto been unable fully to meet the demands made of them in practice. The characteristic difference between the compounds of formula I according to the invention and the known compounds is the introduction of specific substituents and their combination into the anilinopyrimidine structure, as a result of which an unexpectedly high fungicidal activity and insecticidal action is obtained with the novel compounds.

The compounds of formula I are oils, resins or solids that are stable at room temperature and that are distinguished by valuable microbicidal properties. They can be used preventively and curatively in the agricultural sector or related fields for controlling plant-destructive microorganisms. The compound of formula I according to the invention are distinguished in low application concentrations not only by excellent insecticidal and fungicidal actions but also by the fact that they are especially well tolerated by plants.

An important group of phytofungicides is formed by those of the formula I in which $R_1$ and $R_2$ are hydrogen.

A special group of anilinopyrimidine derivatives is formed by compounds of formula I in which $R_1$ and $R_2$ independently of one another are hydrogen, halogen, $C_1$–$C_3$-alkyl, $C_1$–$C_2$-haloalkyl, $C_1$–$C_3$-alkoxy or $C_1$–$C_3$-haloalkoxy;

$R_3$ is hydrogen, $C_1$–$C_4$-alkyl or cyclopropyl;

$R_4$ is $C_1$–$C_8$-alkyl; $C_2$–$C_6$-alkyl substituted by halogen, hydroxy, cyano, $C_1$–$C_4$-alkoxy, $C_3$–$C_4$-alkoxyalkoxy or by $C_1$–$C_3$-alkylthio; $C_3$–$C_6$-alkenyl; $C_3$–$C_6$-alkynyl; $C_5$–$C_7$-cycloalkyl; or Chd $5$–$C_7$-cycloalkyl substituted by methyl; and X is oxygen or sulphur.

The following groups of active ingredients are preferred because of their pronounced biocidal, especially phytofungicidal, activity:

Group 1a: Compounds of formula I in which:

$R_1$ and $R_2$ independently of one another are hydrogen, fluorine, chlorine, bromine, $C_1$–$C_3$-alkyl, $C_1$–$C_2$-haloalkyl, $C_1$–$C_3$-alkoxy or $C_1$–$C_2$-haloalkoxy;

$R_3$ is hydrogen, $C_1$–$C_3$-alkyl or cyclopropyl;

$R_4$ is $C_1$–$C_6$-alkyl; $C_2$–$C_4$-alkyl substituted by halogen, hydroxy, cyano, $C_1$–$C_3$-alkoxy, $C_3$–$C_4$-alkoxyalkoxy or by $C_1$–$C_2$-alkylthio; $C_3$-alkenyl; $C_3$-alkynyl: or by $C_6$–$C_7$-cycloalkyl that is unsubstituted or substituted by methyl; and X is oxygen or sulphur.

Of the above-mentioned compounds, an especially preferred group is formed by those in which $R_1=R_2=$hydrogen (=Group 1aa).

Group 1b: Compounds of formula I in which:

$R_1$ and $R_2$ independently of one another are hydrogen, fluoride, chlorine, bromine, $C_1$–$C_3$-alkyl, $C_1$–$C_3$-alkoxy, trifluoromethyl, $—OCHF_2$, $—OCF_2CHF_2$, $—OCF_2CHClF$, $—OCF_2CHCl_2$ or $—OCF_2CCl_2F$;

$R_3$ is hydrogen, methyl, ethyl or n-propyl;

$R_4$ is $C_1$–$C_4$-alkyl; $C_2$–$C_3$-alkyl substituted by halogen, hydroxy, cyano, $C_1$–$C_2$-alkoxy or by $C_1$–$C_2$-alkylthio; $C_3$–$C_6$-alkenyl; $C_3$–$C_6$-alkynyl; or cyclohexyl; and X is oxygen or sulphur.

Of the above mentioned compounds, an especially preferred group is formed by those in which $R_1=R_2=$hydrogen (=Group 1bb).

Group 1c: Compounds of formula I in which:

$R_1$ and $R_2$ independently of one another are hydrogen, fluorine, chlorine, bromine, $C_1$–$C_2$-alkyl, $C_1$–$C_2$-alkoxy, trifluoromethyl, $—OCHF_2$, $—OCF_3$, $—OCF_2CHF_2$ or $—OCF_2CHClF$;

$R_3$ is a hydrogen or $C_1$–$C_2$-alkyl;

$R_4$ is $C_1$–$C_3$-alkyl; $C_2$-alkyl substituted by halogen, hydroxy, cyano, $C_1$–$C_2$-alkoxy or by $C_1$–$C_2$-alkylthio; $C_3$–$C_4$-alkenyl; or $C_3$–$C_4$-alkynyl; and X is oxygen or sulphur.

Of the above-mentioned compounds, an especially preferred group is formed by those in which $R_1 = R_2 =$ hydrogen and X is oxygen (=Group 1cc).

Group 1d: Compounds of formula I in which:
$R_1$ and $R_2$ independently of one another are hydrogen, fluorine, chlorine, bromine, $C_1$-$C_2$-alkyl, $C_1$-$C_2$-alkoxy, trifluoromethyl or $-OCHF_2$;
$R_3$ is methyl;
$R_4$ is $C_1$-$C_2$-alkyl; $C_2$-alkyl substituted by fluorine, chlorine, bromine, cyano, $C_1$-$C_2$-alkoxy or by methylthio; allyl; or propargyl; and
X is oxygen or sulphur.

Of the above-mentioned compounds, an especially preferred group is formed by those in which $R_1 = R_2 =$ hydrogen and X is oxygen (=Group 1dd).

Group 2a: Compounds of formula I in which:
$R_1$ and $R_2$ independently of one another are hydrogen, halogen, $C_1$-$C_2$-alkyl, halomethyl, $C_1$-$C_2$-alkoxy or $C_1$-$C_2$-haloalkoxy;
$R_3$ is hydrogen; $C_1$-$C_3$-alkyl; $C_1$-$C_2$-alkyl substituted by halogen or by hydroxy; cyclopropyl; or cyclopropyl mono- to tri-substituted by the same or different substituents selected from the group consisting of halogen and methyl;
$R_4$ is $C_1$-$C_4$-alkyl; $C_2$-$C_3$-alkyl substituted by halogen, cyano, $C_1$-$C_2$-alkoxy or by $C_1$-$C_2$-alkylthio; $C_3$-$C_6$-alkenyl; $C_3$-$C_6$-alkynyl; or $C_3$-$C_7$-cycloalkyl: and
X is oxygen or sulphur.

Of the above-mentioned compounds, an especially preferred group is formed by those in which $R_1 = R_2 =$ hydrogen (=Group 2aa).

Group 2b: Compounds of formula I in which:
$R_1$ and $R_2$ independently of one another are hydrogen, fluorine, chlorine, bromine, methyl, trifluoromethyl, methoxy or difluoromethoxy;
$R_3$ is hydrogen; $C_1$-$C_3$-alkyl; $C_1$-$C_2$-alkyl substituted by halogen or by hydroxy; cyclopropyl; or cyclopropyl mono- to tri-substituted by the same or different substituents selected from the group consisting of halogen and methyl;
$R_4$ is $C_1$-$C_3$-alkyl; $C_2$-$C_3$-alkyl substituted by fluorine, chlorine or by $C_1$-$C_2$-alkoxy; $C_3$-$C_6$-alkenyl; $C_3$-$C_6$-alkynyl; or $C_3$-$C_6$-cycloalkyl; and
X is oxygen or sulphur.

Of the above-mentioned compounds, an especially preferred group is formed by those in which $R_1 = R_2 =$ hydrogen (=Group 2bb).

Group 2c: Compounds of formula I in which:
$R_1$ and $R_2$ independently of one another are hydrogen, fluorine, chlorine, methyl, trifluoromethyl, methoxy or difluoromethoxy;
$R_3$ is $C_1$-$C_3$-alkyl; methyl substituted by halogen or by hydroxy; cyclopropyl; or cyclopropyl mono- to tri-substituted by halogen or by methyl;
$R_4$ is $C_1$-$C_3$-alkyl; $C_2$-$C_3$-alkyl substituted by fluorine, chlorine or by methoxy; $C_3$-$C_4$-alkenyl; $C_3$-$C_4$-alkynyl; cyclopropyl; or cyclohexyl; and
X is oxygen.

Of the above-mentioned compounds, an especially preferred group is formed by those in which $R_1 = R_2 =$ hydrogen (=Group 2cc).

Group 2d: Compound of formula I in which:
$R_1$ and $R_2$ are hydrogen;
$R_3$ is $C_1$-$C_3$-alkyl; methyl substituted by fluorine, chlorine or by bromine; cyclopropyl; or cyclopropyl substituted by chlorine or by methyl;
$R_4$ is $C_1$-$C_3$-alkyl; 2-chloroethyl, 2,2,2-trifluoroethyl, allyl or propargyl; and X is oxygen.

Individual substances that are especially preferred are, for example:
2-phenylamino-4-methyl-6-methoxymethylpyrimidine (comp. no. 1);
2-phenylamino-4-cyclopropyl-6-methoxymethylpyrimidine (comp. no. 10).

The compounds of formula I are prepared as follows:
1. a phenylguanidine salt of formula IIa

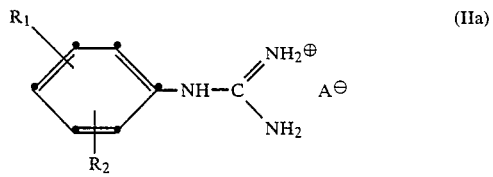

or the free guanidine base of formula IIb

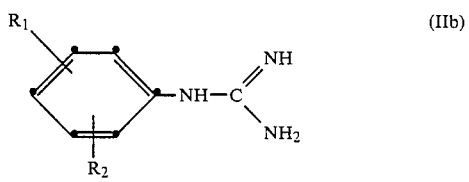

is reacted with a diketone of formula III

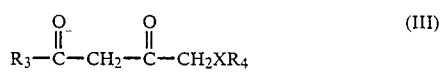

without solvents or in an aprotic solvent, but preferably in a protic solvent, at temperatures of from 60° C. to 160° C., preferably from 60° C. to 110° C., or 2. in a multi-stage process:
2.1 urea of formula IV

is reacted with a diketone of formula III

in the presence of an acid in an inert solvent at temperatures of from 20° C. to 140° C., preferably from 40° C. to 100° C., and is then cyclised at the reflux temperature of the solvent used to give a pyrimidine compound of formula V

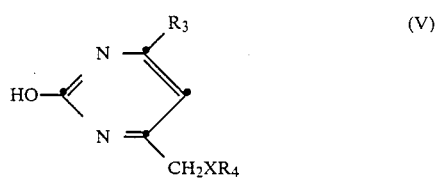

and
2.2 the resulting compound of formula V is reacted further with excess $POCl_3$, without solvents or in a solvent that is inert towards POCl₃, at temperatures of from 50° C. to 110° C., preferably at the reflux temperature of POCl₃, to give the compound of formula VI

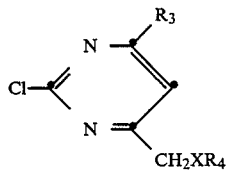     (VI)

and 2.3 the resulting compound of formula VI is reacted further with an aniline compound of formula VII

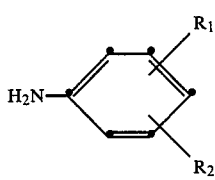     (VII)

depending on the reaction conditions either (a) in the presence of a proton acceptor, such as an excess of the aniline compound of formula VII or an inorganic base, without solvents or in a protic or aprotic solvent, or (b) in the presence of an acid in an inert solvent, in each case at temperatures of from 60° C. to 120° C., preferably from 80° C. to 100° C.; or 3. in a two-stage process:

3.1 a guanidinium salt of formula VIII

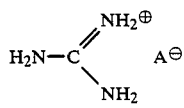     (VIII)

is cyclised with a diketone of formula III

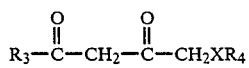     (III)

(a) without solvents, at temperatures of from 100° C. to 160° C., preferably from 120° C. to 150° C., or (b) in a protic or aprotic solvent or a mixture of protic and aprotic solvents, at temperatures of from 30° C. to 140° C., preferably from 60° C. to 120° C., to give a pyrimidine compound of formula IX

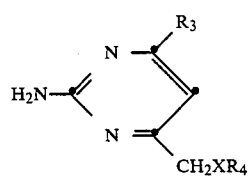     (IX)

and 3.2 the resulting compound of formula IX is reacted with a compound of formula X

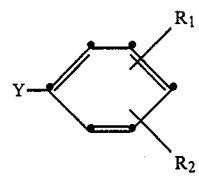     (X)

in the presence of a proton acceptor in aprotic solvents at temperatures of from 30° C. to 140° C., preferably from 60° C. to 120° C., to remove HY, the substituents R₁ to R₄ and X in the formulae II to X being as defined for formula I, A⊖ being an acid anion and Y being halogen.

In the processes described above, in the case of compounds of formulae IIa and VIII containing the acid anion A⊖, the following salts, for example, are suitable: carbonate, hydrogen carbonate, nitrate, halide, sulphate and hydrogen sulphate. Halide is to be understood as meaning fluoride, chloride, bromide or iodide, preferably chloride or bromide.

The acids used are especially inorganic acids such as, for example, hydrohalic acids, for example hydrofluoric acid, hydrochloric acid or hydrobromic acid, and also sulphuric acid, phosphoric acid or nitric acid; however, suitable organic acids may also be used.

As proton acceptors there are used, for example, inorganic bases, such as, for example, alkali metal or alkaline earth metal compounds, for example the hydroxides, oxides or carbonates of lithium, sodium, potassium, magnesium, calcium, strontium and barium, or also hydrides, such as, for example, sodium hydride.

In the processes described above, for example, the following solvents may be used, depending on the particular reaction conditions:

Halogenated hydrocarbons, especially chlorinated hydrocarbons, such as tetrachloroethylene, tetrachloroethane, dichloropropane, methylene chloride, dichlorobutane, chloroform, chloronaphthalene, carbon tetrachloride, trichloroethane, trichloroethylene, pentachloroethane, difluorobenzene, 1,2-dichloroethane, 1,1-dichloroethane, 1,2-cis-dichloroethylene, chlorobenzene, fluorobenzene, bromobenzene, dichlorobenzene, dibromobenzene, chlorotoluene, trichlorotoluene; ethers, such as ethyl propyl ether, methyl tert.-butyl ether, n-butyl ethyl ether, di-n-butyl ether, diisobutyl ether, diisoamyl ether, diisopropyl ether, anisole, cyclohexyl methyl ether, diethyl ether, ethylene glycol dimethyl ether, tetrahydrofuran, dioxan, thioanisole, dichlorodiethyl ether; nitro-hydrocarbons, such as nitromethane, nitroethane, nitrobenzene, chloronitrobenzene, o-nitrotoluene; nitriles, such as acetonitrile, butyronitrile, isobutyronitrile, benzonitrile, m-chlorobenzonitrile; aliphatic or cycloaliphatic hydrocarbons, such as heptane, hexane, octane, nonane, cymol, petroleum fractions within a boiling point range of from 70° C. to 190° C., cyclohexane, methylcyclohexane, Decalin, petroleum ether, ligroin, trimethylpentane, such as 2,3,3-trimethylpentane; esters, such as ethyl acetate, ethyl acetoacetate, isobutyl acetate,; amides, for example formamide, methylformamide, dimethylformamide; ketones, such as acetone, methyl ethyl ketone; alcohols, especially lower aliphatic alcohols, such as, for example, methanol, ethanol, n-propanol, isopropanol and the butanols; and, where appropriate, also water. Also suitable are mixtures of the above mentioned solvents and diluents.

Methods of synthesis that are analogous to the abovementioned preparation processes have been published in the literature in the following references:

Process 1: A. Kreutzberger and J. Gillessen, J. Heterocyclic Chem. 22, 101 (1985).

Process 2, Stage 2.1: O. Stark, Ber. Dtsch. Chem. Ges. 42, 699 (1909); J. Hale, J. Am. Chem. Soc. 36, 104 (1914); G. M. Kosolapoff, J. Org. Chem. 26, 1895 (1961). Stage 2.2; St. Angerstein, Ber. Dtsch. Chem. Ges. 34, 3956 (1901); G. M. Kosolapoff, J. Org. Chem. 26, 1895 (1961). Stage 2.3; M. P. V. Boarland and J. F. W. McOmie, J. Chem. Soc. 1951, 1218; T. Matsukawa and K. Shirakuwa, J. Pharm. Soc. Japan 71, 933 (1951); Chem. Abstr. 46, 4549 (1952).

Process 3: A. Combes and C. Combes, Bull Soc. Chem. (3), 7, 791 (1892); W. J. Hale and F. C. Vibrans, J. Am. Chem. Soc. 40, 1046 (1918).

The described preparation processes, including all partial steps, form part of the present invention.

Surprisingly, it has been found that the compounds of formula I have, for practical field application purposes, a very advantageous biocidal spectrum against insects and phytopathogenic microorganisms, especially fungi. Compounds of formula I have very advantageous curative, preventive and, in particular, systemic properties, and can be used for protecting numerous cultivated plants. With the compounds of formula I it is possible to inhibit or destroy the pests which occur in plants or in parts of plants (fruit, blossoms, leaves, stems, tubers, roots) in different crops of useful plants, while at the same time the parts of plants which grow later are also protected, for example, from attack by phytopathogenic microorganisms.

The compounds of formula I are effective against phytopathogenic fungi belonging to the following classes: Fungi imperfecti (e.g. Botrytis, Helminthosporium, Fusarium, Septoria, Cercospora, Alternaria); Basidiomycetes (e.g. the genera Hemileia, Rhizoctonia, Puccinia); and Ascomycetes (e.g. Venturia, Podosphaera, Erysiphe, Monilinia, Uncinula). They are also effective against Oomycetes (Perenosporales, Phytophthora, Plasmopara, Pythium). They can be used as dressing agents for protecting seeds (fruit, tubers, grains) and plant cuttings against fungus infections as well as against phytopathogenic fungi which occur in the soil. In addition, compounds of formula I are effective against insect pests, for example against pests on cereals such as rice.

The invention also relates to compositions containing as active ingredient compounds of formula I, especially plant-protecting compositions, and to their use in the agricultural sector or related fields.

The present invention further embraces the preparation of those compositions, which comprises homogeneously mixing the active ingredient with one or more compounds or groups of compounds described herein. The invention furthermore relates to a method of treating plants, which comprises applying thereto the novel compounds of formula I or the novel compositions.

Target crops to be protected within the scope of the present invention comprise e.g. the following species of plants: cereals (wheat, barley, rye, oats, rice, maize, sorghum and related crops), beets (sugar beet and fodder beet), pomes, drupes and soft fruit (apples, pears, plums, peaches, almonds, cherries, strawberries, raspberries, and blackberries), leguminous plants (beans, lentils, peas, soybeans), oil plants (rape, mustard, poppy, olives, sunflowers, coconut, castor oil plants, cocoa beans, groundnuts), cucumber plants (cucumber, marrows, melons), fibre plants (cotton, flax, hemp, jute), citrus fruit (oranges, lemons, grapefruit, mandarins), vegetables (spinach, lettuce, asparagus, cabbages, carrots, onions, tomatoes, potatoes, paprika), lauraceae (avocados, cinnamon, camphor), or plants such as tobacco, nuts, coffee, sugar cane, tea, pepper, vines, hops, bananas and natural rubber plants as well as ornamentals.

The compounds of formula I are normally applied in the form of compositions and can be applied to the crop area or plant to be treated, simultaneously or in succession, with further compounds. These compounds can be fertilisers or micronutrient donors or other preparations that influence plant growth. They can also be selective herbicides, insecticides, fungicides, bactericides, nematicides, molluscicides or mixtures of several of these preparations, if desired together with further carriers, surfactants or application-promoting adjuvants customarily employed in the art of formulation.

Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilisers.

A preferred method of applying a compound of formula I, or an agrochemical composition which contains at least one of said compounds, is foliar application. The number of applications and the rate of application depend on the risk of infestation by the corresponding pathogen. However, the compounds of formula I can also penetrate the plant through the roots via the soil (systemic action) if the locus of the plant is impregnated with a liquid formulation, or if the compounds are applied in solid form to the soil, e.g. in granular form (soil application). In paddy rice crops, such granulates may be applied in metered amounts to the flooded rice field. The compounds of formula I may, however, also be applied to seeds (coating) by impregnating the seeds either with a liquid formulation containing a compound of formula I, or coating them with a solid formulation.

The compounds of formula I are used in unmodified form or, preferably, together with the adjuvants conventionally employed in the art of formulation, and are for this purpose advantageously formulated in known manner e.g. into emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering, coating or pouring, are chosen in accordance with the intended objectives and the prevailing circumstances. Advantageous rates of application are normally from 50 g to 5 kg of active ingredient (a.i.) per hectare, preferably from 100 g to 2 kg a.i./ha, most preferably from 200 g to 600 g a.i./ha.

The formulations, i.e. the compositions, preparations or mixtures containing the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulphoxide or dimethylformamide, as well as vegetable oils or epoxidised vegetable oils, such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of pregranulated materials of inorganic nature can be used, e.g. especially dolomite or pulverised plant residues. Particularly advantageous application-promoting adjuvants which are able to reduce substantially the rate of application are also natural (animal or vegetable) or synthetic phospholipids of the series of the cephalins and lecithins, which can be obtained e.g. from soybeans.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and also water-soluble synthetic surface-active compounds are suitable anionic surfactants.

Suitable soaps are the alkali metals salts, alkaline earth metal salts or unsubstituted or substituted ammonium salts of higher fatty acids ($C_{10}$–$C_{22}$), e.g. the sodium or potassium salts of oleic or stearic acid or of natural fatty acid mixtures which can be obtained e.g. from coconut oil or tallow oil. Mention may also be made of fatty acid methyllaurin salts.

More frequently, however, so-called synthetic surfactants are used, especially alkanesulphonates, fatty alcohol, sulphates, sulphonated benzimidazole derivatives or alkylsulphonates.

The fatty alcohol sulphonates or sulphates are usually in the form of alkali metal salts, alkaline earth metal salts or unsubstituted or substituted ammonium salts and contain a $C_8$–$C_{22}$-alkyl radical which also includes the alkyl moiety of acyl radicals, e.g. the sodium of calcium salt of lignosulphonic acid, of dodecylsulphate or a mixture of fatty alcohols sulphates obtained from natural fatty acids. These compounds also comprise the salts of sulphated and sulphonated fatty alcohol/ethylene oxide adducts. The sulphonated benzimidazole derivatives preferably contain 2 sulphonic acid groups and one fatty acid radical containing 8 to 22 carbon atoms. Examples of alkylarylsulfonates are the sodium, calcium or triethanolamine salts of dodecylbenzenesulphonic acid, dibutylnaphthalenesulfonic acid, or of a condensate of naphthalenesulphonic acid and formaldehyde.

Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contains 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethyleneethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$-alkyl radical and, as further substituents, unsubstituted or halogenated lower alkyl, benzyl or hydroxy-lower alkyl radicals. The salts are preferably in the form of halides, methylsulphates or ethylsulphates, e.g. stearyltrimethylammonium chloride or benzyldi(2-chloroethyl)ammonium bromide.

Further surfactants customarily employed in the art of formulation are know to the person skilled in the art or can be taken from the relevant specialist literature.

The agrochemical compositions usually contain 0.1 to 99% by weight, preferably 0.1 to 95% by weight, of a compound of formula I, 99.9 to 1% by weight, preferably 99.8 to 5% by weight, of a solid or liquid adjuvant, and 0 to 25% by weight, preferably 0.1 to 25% by weight, of a surfactant.

Whereas commercial products will preferably by formulated as concentrates, the end user will normally employ dilute formulations.

The compositions may also contain further auxiliaries such as stabilisers, antifoams, viscosity regulators, binders, tackifiers as well as fertilisers or other active ingredients for obtaining special effects.

The following Examples serve to illustrate the invention in greater detail, without limiting it.

EXAMPLE 1

Preparation of 2-phenylamino-4-methyl-6-methoxymethylpyrimidine

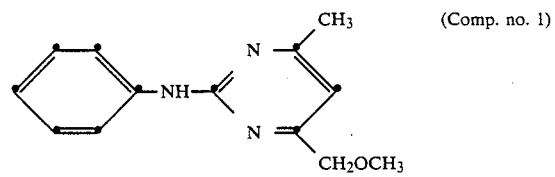

(Comp. no. 1)

A mixture of 7.5 g of phenylguanidine hydrogen carbonate and 7.4 g of methoxyacetylacetone is heated at 100° C. for four hours with stirring, the evolution of carbon dioxide which occurs subsiding as the reaction progresses. After the brown emulsion has been cooled to room temperature, 60 ml of diethyl ether are added and the whole is then washed three times with 20 ml of water each time, dried over sodium sulphate and filtered, and the solvent is evaporated. The 10.5 g of oily residue are dissolved in 140 ml of diethyl ether, and then 4.4 g of 65% nitric acid are added thereto with stirring. The suspension of the resulting nitrate salt is stirred for a further 20 minutes and is then filtered and washed with 100 ml of diethyl ether. 6 g of 30% sodium hydroxide solutions are added with stirring to a mixture consisting of 11 g of the nitrate sale, 80 ml of diethyl ether and 60 ml of water, the organic phase is separated off, washed twice with 40 ml of water each time, dried over sodium sulfate and filtered, and the solvent is evaporated. The 8.7 g of light-brown oily residue are crystallised with 100 ml of petroleum ether (b.p. 50°–70° C.), filtered and dried. The 8 g of pale, beige-coloured crystalline powder melt at 59°–60° C.; yield: 92% of the theoretical yield, relative to phenylguanidine hydrogen carbonate.

EXAMPLE 2

Preparation of 2-(p-chlorophenylamino)-4-methyl-6-methoxymethyl-pyrimidine (Comp. no. 70)

A solution of 6.4 g of 4-chloroaniline and 8.6 g of 2-chloro-4-methyl-6-methoxymethylpyrimidine is adjusted to pH 1 with 5 ml of concentrated hydrochloric acid with stirring, and is then heated under reflux for 20 hours. After cooling to room temperature, the brown emulsion is rendered alkaline with 12 ml of 30% ammonia, poured onto 100 ml of icewater and extracted three times with 50 ml of ethyl acetate each time. The combined extracts are washed with 50 ml of water, dried over sodium sulphate and filtered, and the solvent is evaporated. The 11.8 g of red oil are chromatographed over a 30 cm long silica gel column using dichloromethane/diethyl ether (3:2). After evaporation of the eluant, the initially oily residue is crystallised by trituration with petroleum ether. Recrystallisation from diisopropyl ether/petroleum ether (50°–70° C.) gives 9.8 g of beige-coloured crystalline powder which melts at 57°–59° C.; yield: 74% of the theoretical yield.

TABLE

Compounds of the formula

| Comp. No. | $R_1$ | $R_2$ | $R_3$ | X | $R_4$ | Physical data |
|---|---|---|---|---|---|---|
| 1 | H | H | $CH_3$ | O | $-CH_3$ | m.p. 59–60° C. |
| 2 | H | H | $CH_3$ | O | $-CH_2CH=CH_2$ | oil $n_D^{24}$ 1.6013 |
| 3 | H | H | $CH_3$ | O | $-C_2H_5$ | oil $n_D^{24}$ 1.5975 |
| 4 | H | H | $C_4H_9$—tert. | O | $-CH_3$ | m.p. 71,5–73° C. |
| 5 | H | H | $CH_3$ | O | $-CH_2-C\equiv CH$ | oil $n_D^{24}$ 1.6106 |
| 6 | H | H | $CH_3$ | O | $-C_3H_7-n$ | $n_D^{24}$ 1.5880 |
| 7 | H | H | $CH_3$ | S | $-CH_3$ | oil $n_D^{25}$ 1.6452 |
| 8 | H | H | $C_4H_9$—tert. | O | $-C_2H_5$ | viscous composition $n_D^{25}$ 1.5717 |
| 9 | 3-Cl | 5-Cl | $CH_3$ | O | $-CH_2-C\equiv CH$ | m.p. 88–91° C. |
| 10 | H | H | cyclopropyl | O | $-CH_3$ | m.p. 79–80° C. |
| 11 | H | H | $CH_3$ | O | $-C_3H_7-i$ | oil $n_D^{24}$ 1.5919 |
| 12 | 4-$OCH_3$ | H | $CH_3$ | O | $-CH_3$ | m.p. 57–59° C. |
| 13 | 3-$OC_2H_5$ | 4-$OC_2H_5$ | $CH_3$ | O | $-C_2H_5$ | red oil $n_D^{24}$ 1.5936 |
| 14 | H | H | $CH_3$ | O | $-C_4H_9-n$ | |
| 15 | H | H | $CH_3$ | O | $-CHC_2H_5$ with $CH_3$ | oil $n_D^{25}$ 1.5788 |
| 16 | H | H | $CH_3$ | O | $-CH_2-C(CH_3)=CH_2$ | |
| 17 | 3-$OC_2H_5$ | 4-$OC_2H_5$ | $CH_3$ | O | $-CH_3$ | m.p. 54–57° C. |

TABLE-continued

Compounds of the formula

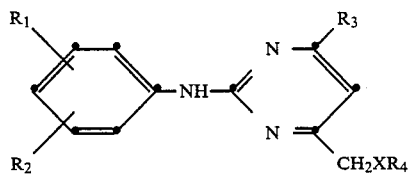

| Comp. No. | R₁ | R₂ | R₃ | X | R₄ | Physical data |
|---|---|---|---|---|---|---|
| 18 | H | H | $CH_3$ | O | $-CH_2CH(CH_3)_2$ | oil $n_D^{24}$ 1.5813 |
| 19 | 3-Cl | 5-Cl | $CH_3$ | O | $-C_2H_5$ | oil $n_D^{24}$ 1.5963 |
| 20 | H | H | $CH_3$ | S | $-C_2H_5$ | |
| 21 | 3-Cl | 5-Cl | $CH_3$ | O | $-CH_2CH=CH_2$ | oil $n_D^{24}$ 1.6078 |
| 22 | 4-$OCH_3$ | H | cyclopropyl | O | $-CH_3$ | viscous composition $n_D^{24}$ 1.6109 |
| 23 | H | H | $CH_3$ | O | $-C(CH_3)_3$ | |
| 24 | H | H | $CH_3$ | O | $-CH_2CH_2OCH_3$ | oil $n_D^{24}$ 1.6011 |
| 25 | 3-Cl | 5-Cl | $CH_3$ | O | $-CH_3$ | viscous composition $n_D^{24}$ 1.6180 |
| 26 | H | H | $CH_3$ | O | $-(CH_2)_4CH_3$ | |
| 27 | 4-$OCH_3$ | H | $CH_3$ | O | $-C_2H_5$ | oil $n_D^{24}$ 1.5838 |
| 28 | H | H | $CH_3$ | O | $-CH(CH_3)-C\equiv CH$ | |
| 29 | 3-$OC_2H_5$ | 4-$OC_2H_5$ | cyclopropyl | O | $-CH_3$ | black oil |
| 30 | H | H | $CH_3$ | O | $-CH(CH_3)-C_3H_7-n$ | |
| 31 | 3-$OC_2H_5$ | 4-$OC_2H_5$ | $CH_3$ | O | $-CH_2CH=CH_2$ | black oil |
| 32 | H | H | $CH_3$ | O | $-CH_2CH_2OC_2H_5$ | |
| 33 | H | H | $CH_3$ | O | $-CH_2CH(CH_3)-C_2H_5$ | |
| 34 | 3-Cl | 5-Cl | cyclopropyl | O | $-CH_3$ | viscous composition $n_D^{24}$ 1.6228 |
| 35 | 4-$OCH_3$ | H | $CH_3$ | O | $-CH(CH_3)C_2H_5$ | oil $n_D^{24}$ 1.5760 |
| 36 | H | H | $CH_3$ | O | $-C(CH_3)_2-CH=CH_2$ | |
| 37 | 3-Cl | 5-Cl | $CH_3$ | O | $-CH(CH_3)-C_2H_5$ | viscous composition $n_D^{24}$ 1.5879 |
| 38 | H | H | $C_2H_5$ | O | $-CH_3$ | m.p. 35,5–37° C. |
| 39 | H | H | $CH_3$ | O | $-CH_2CH_2CH(CH_3)CH_3$ | |
| 40 | H | H | $CH_3$ | O | $-CH_2CF_3$ | oil $n_D^{25}$: 1.6205 |
| 41 | 3-$OC_2H_5$ | 4-$OC_2H_5$ | $CH_3$ | O | $-CH(CH_3)C_2H_5$ | dark red oil $n_D^{25}$ 1.6205 |
| 42 | H | H | $CH_3$ | O | $-CH_2CH_2-C(CH_3)=CH_2$ | |
| 43 | H | H | $CH_3$ | O | $-CH_2CH_2OCH(CH_3)CH_3$ | |

TABLE-continued

Compounds of the formula

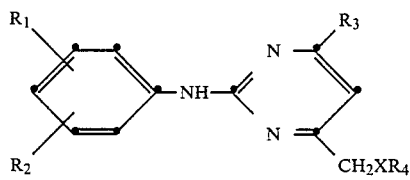

| Comp. No. | R₁ | R₂ | R₃ | X | R₄ | Physical data |
|---|---|---|---|---|---|---|
| 44 | 4-OCH₃ | H | C₄H₉—tert. | O | —C₂H₅ | viscous composition $n_D^{24}$ 1.5662 |
| 45 | H | H | CH₃ | O | —CH₂—C(CH₃)₂—CH₃ | |
| 46 | H | H | CH₃ | O | —CH₂CH₂O(CH₂)₃CH₃ | |
| 47 | 4-OCH₃ | H | CH₃ | O | —CH₂C≡CH | oil $n_D^{24}$ 1.6059 |
| 48 | H | H | CH₃ | O | —C(CH₃)(C₂H₅)CH₃ | |
| 49 | 3-OC₂H₅ | 4-OC₂H₅ | CH₃ | O | —CH₂—C≡CH | m.p. 63–65° C. |
| 50 | H | H | CH₃ | S | —CH(CH₃)CH₂CH₃ | |
| 51 | H | H | C₂H₅ | O | —C₂H₅ | |
| 52 | H | H | CH₃ | O | cyclopentyl | |
| 53 | 3-Cl | 5-Cl | C₄H₉—tert. | O | —C₂H₅ | oil $n_D^{24}$ 1.5848 |
| 54 | 3-OC₂H₅ | 4-OC₂H₅ | C₄H₉—tert. | O | —C₂H₅ | black oil |
| 55 | H | H | CH₃ | O | —CH(CH₃)—CH(CH₃)—CH₃ | |
| 56 | H | H | CH₃ | O | —CH₂CH₂CN | |
| 57 | H | H | CH₃ | O | cyclohexyl | |
| 58 | H | H | CH₃ | O | —CH₂CH₂O(CH₂)₂OCH₃ | |
| 59 | H | H | cyclopropyl | O | —C₂H₅ | m.p. 54–57° C. |
| 60 | H | H | CH₃ | O | —(CH₂)₅CH₃ | |
| 61 | H | H | C₂H₅ | O | —CH₂—CH=CH₂ | |
| 62 | 3-OC₂H₅ | 4-OC₂H₅ | C₄H₉—tert. | O | —CH₃ | viscous composition |
| 63 | H | H | CH₃ | O | —CH₂CH(CH₃)—C₃H₇—n | |
| 64 | H | H | CH₃ | O | —CH₂CH₂OH | |
| 65 | H | H | CH₃ | O | cycloheptyl | |
| 66 | H | H | CH₃ | O | —C(CH₃)₂CN | |
| 67 | H | H | cyclopropyl | O | —CH₂—CH=CH₂ | |
| 68 | H | H | CH₃ | O | —CH₂CH(C₂H₅)—C₂H₅ | |
| 69 | 4-OCH₃ | H | C₄H₉—tert. | O | —CH₃ | m.p. 104–106° C. |
| 70 | 4-Cl | H | CH₃ | O | —CH₃ | m.p. 57–59° C. |
| 71 | H | H | CH₃ | O | —CH(CH₃)—CH₂—CH(CH₃)—CH₃ | |
| 72 | 4-Cl | H | CH₃ | O | —C₂H₅ | |
| 73 | H | H | C₃H₇—i | O | —CH₂CH₂OH | |
| 74 | H | H | CH₃ | O | 2-methylcyclohexyl | |

TABLE-continued

Compounds of the formula

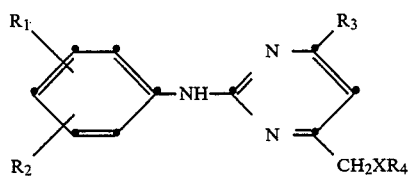

| Comp. No. | $R_1$ | $R_2$ | $R_3$ | X | $R_4$ | Physical data |
|---|---|---|---|---|---|---|
| 75 | H | H | $CH_3$ | O | $-(CH_2)_6OH$ | |
| 76 | H | H | $CH_3$ | O | $-(CH_2)_6CH_3$ | |
| 77 | H | H | cyclopropyl | O | cyclohexyl | |
| 78 | H | H | $CH_3$ | S | $-(CH_2)_5CH_3$ | |
| 79 | H | H | $C_3H_7-i$ | O | $-CH_2CH_2OC_2H_5$ | |
| 80 | H | H | $CH_3$ | O | $-CH(CH_3)(CH_2)_4CH_3$ | |
| 81 | H | H | $CH_3$ | O | $-CH(CN)-CH_3$ | |
| 82 | H | H | $CH_3$ | O | $-CH_2CH_2SCH_3$ | |
| 83 | H | H | $CH_3$ | O | $-CH_2CH(OH)-CH_3$ | |
| 84 | 4-Cl | H | $CH_3$ | O | $-CH_2CH=CH_2$ | |
| 85 | H | H | $C_2H_5$ | O | $-CH_2-C(CH_3)=CH_2$ | |
| 86 | H | H | $C_3H_7-n$ | O | $-CH_2-C\equiv CH$ | |
| 87 | H | H | $CH_3$ | O | $-CH(C_2H_5)-(CH_2)_3CH_3$ | |
| 88 | H | H | $CH_3$ | S | $-CH(CH_3)-CH_3$ | |
| 89 | H | H | $C_3H_7-i$ | O | $-CH_2CH_2OCH_3$ | |
| 90 | H | H | $CH_3$ | O | $-CH_2CH_2Cl$ | |
| 91 | H | H | $C_3H_7-i$ | O | $-CH_2-C\equiv CH$ | |
| 92 | H | H | $CH_3$ | O | $-CH(C_3H_7-n)-CH_2CH_2CH_3$ | |
| 93 | 4-Cl | H | $CH_3$ | O | $-CH_2OCH_2CH_2OCH_3$ | |
| 94 | H | H | $CH_3$ | S | $-CH_2-CH=CH_2$ | |
| 95 | H | H | $C_2H_5$ | O | $-CH_2-C\equiv CH$ | |
| 96 | H | H | $CH_3$ | O | $-(CH_2)_3Cl$ | |
| 97 | 4-Cl | H | $CH_3$ | O | $-CH_2CF_3$ | |
| 98 | H | H | $CH_3$ | O | $-(CH_2)_7CH_3$ | |
| 99 | 4-Cl | H | $C_2H_5$ | O | $-CH_3$ | |
| 100 | 3-Cl | H | $CH_3$ | O | $-CH_3$ | m.p. 49-51° C. |
| 101 | H | H | $CH_3$ | S | $-CH_2-CH(CH_3)-CH_3$ | |
| 102 | 4-Cl | H | H | O | $-CH_3$ | |
| 103 | H | H | $C_3H_7-i$ | O | $-CH_2-CH=CH_2$ | |
| 104 | 4-Br | H | $CH_3$ | O | $-CH_3$ | m.p. 76-78° C. |
| 105 | H | H | $CH_3$ | O | $-CH(CH_3)(CH_2)_5CH_3$ | |
| 106 | 4-Cl | H | $CH_3$ | O | $-CH_2-C\equiv CH$ | |
| 107 | H | H | $C_2H_5$ | O | cyclohexyl | |
| 108 | H | H | $CH_3$ | O | $-(CH_2)_4Cl$ | |
| 109 | 4-Br | H | $CH_3$ | O | $-C_2H_5$ | |
| 110 | H | H | $C_3H_7-i$ | O | $-CH_2CH_2Cl$ | |

TABLE-continued

Compounds of the formula

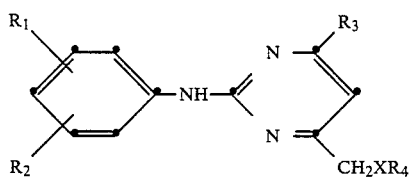

| Comp. No. | $R_1$ | $R_2$ | $R_3$ | X | $R_4$ | Physical data |
|---|---|---|---|---|---|---|
| 111 | 4-Br | H | $CH_3$ | O | $-CH_2CF_3$ | |
| 112 | H | H | $CH_3$ | O | $-CH(CH_2Cl)_2$ | |
| 113 | H | H | cyclopropyl | O | $-CH_2CH_2OC_2H_5$ | |
| 114 | H | H | $C_3H_7-i$ | O | $-(CH_2)_4CH_3$ | |
| 115 | H | H | $C_3H_7-i$ | O | $-CH_2CF_3$ | |
| 116 | H | H | $C_2H_5$ | O | $-CH_2CH_2OCH_3$ | |
| 117 | 4-Br | H | $CH_3$ | O | $-CH_2CH_2OCH_3$ | |
| 118 | H | H | $C_3H_7-i$ | S | $-CH_3$ | |
| 119 | H | H | $CH_3$ | O | $-CH(CH_3)-CH_2Cl$ | |
| 120 | 3-Cl | H | $CH_3$ | O | $-C_2H_5$ | |
| 121 | H | H | $CH_3$ | O | $-CH_2CCl_3$ | |
| 122 | H | H | $C_3H_7-i$ | O | $-CH(CH_3)C_2H_5$ | |
| 123 | H | H | H | S | $-CH_3$ | |
| 124 | H | H | $C_2H_5$ | O | $-CH_2CH_2OC_2H_5$ | |
| 125 | 4-Br | H | $CH_3$ | O | $-CH_2C\equiv CH$ | |
| 126 | H | H | $C_4H_9-n$ | O | $-CH_3$ | oil $n_D^{24}$ 1.5823 |
| 127 | H | H | $CH_3$ | O | $-CH_2CH_2Br$ | |
| 128 | H | H | $C_3H_7-i$ | O | $-C_2H_5$ | |
| 129 | 4-Br | H | $C_2H_5$ | O | $-CH_3$ | |
| 130 | H | H | $CH_3$ | O | $-(CH_2)_3Br$ | |
| 131 | 3-Cl | H | $CH_3$ | O | $-CH_2CF_3$ | |
| 132 | H | H | H | O | $-CH_2CH_2CN$ | |
| 133 | 3-Cl | H | $CH_3$ | O | $-CH_2CH_2OCH_3$ | |
| 134 | 3-Cl | H | $CH_3$ | O | $-CH_2-CH=CH_2$ | |
| 135 | H | H | $C_3H_7-i$ | O | $-CH_3$ | oil $n_D^{24}$ 1.5883 |
| 136 | H | H | $C_4H_9-n$ | O | $-C_2H_5$ | |
| 137 | H | H | H | O | $-CH_2CH_2Cl$ | |
| 138 | 4-F | H | $CH_3$ | O | $-CH_3$ | m.p. 62-65° C. |
| 139 | H | H | $C_2H_5$ | O | $-CH_2CH_2OH$ | |
| 140 | 3-Cl | H | $CH_3$ | O | $-CH_2-C\equiv CH$ | |
| 141 | H | H | $C_4H_9-n$ | | $-CH(CH_3)C_2H_5$ | |
| 142 | H | H | $C_3H_7-i$ | S | $-CH_3$ | |
| 143 | 3-Cl | 4-Cl | $CH_3$ | O | $-CH_3$ | |
| 144 | H | H | $C_4H_9-n$ | O | $-CH_2CH_2Cl$ | |
| 145 | H | H | H | O | $-CH_2CH_2OH$ | |
| 146 | H | H | $C_2H_5$ | O | $-CH_2CH_2Cl$ | |
| 147 | 3-$CF_3$ | 4-Cl | $CH_3$ | O | $-CH_3$ | m.p. 86-88° C. |
| 148 | H | H | $C_4H_9-n$ | O | $-CH_2CF_3$ | |
| 149 | 3-Cl | 4-Cl | $CH_3$ | O | $-C_2H_5$ | |
| 150 | H | H | $C_3H_7-n$ | O | $-CH_2CH_2CN$ | |
| 151 | 3-Cl | 4-Cl | $CH_3$ | O | $-CH_2-C\equiv CH$ | |
| 152 | H | H | H | O | $-CH_2CH_2OCH_3$ | |
| 153 | 4-$CH_3$ | H | $CH_3$ | O | $-CH_3$ | m.p. 58-60° C. |
| 154 | H | H | $C_2H_5$ | O | $-CH_2CF_3$ | |
| 155 | 3-$CF_3$ | 4-Cl | $CH_3$ | O | $-C_2H_5$ | |
| 156 | H | H | H | O | $-CH_2CH_2OC_2H_5$ | |
| 157 | 3-Cl | 4-Cl | $CH_3$ | O | $-CH_2CF_3$ | |
| 158 | H | H | H | O | cyclohexyl | |
| 159 | H | H | $C_3H_7-n$ | O | $-CH_2CF_3$ | |
| 160 | H | H | cyclopropyl | O | $-CH_2CH_2OCH_3$ | |
| 161 | 3-$CF_3$ | 4-Cl | $CH_3$ | O | $-CH_2C\equiv CH$ | |
| 162 | H | H | $C_2H_5$ | O | $-CH_2CH_2CN$ | |

TABLE-continued

Compounds of the formula

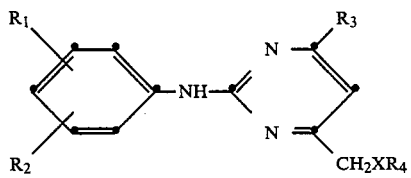

| Comp. No. | R₁ | R₂ | R₃ | X | R₄ | Physical data |
|---|---|---|---|---|---|---|
| 163 | 4-OCHF₂ | H | CH₃ | O | —CH₃ | |
| 164 | H | H | C₄H₉—n | O | —CH₂—C≡CH | |
| 165 | 4-CH₃ | H | CH₃ | O | —C₂H₅ | |
| 166 | 4-CH₃ | H | CH₃ | O | —CH₂C≡CH | |
| 167 | H | H | C₃H₇—n | O | —CH₂CH₂Cl | |
| 168 | H | H | H | O | —CH₂C≡CH | |
| 169 | 4-OCHF₂ | H | CH₃ | O | —C₂H₅ | |
| 170 | H | H | cyclopropyl | O | —CH₂CH₂OH | |
| 171 | H | H | C₂H₅ | S | —CH₃ | |
| 172 | 4-CH₃ | H | CH₃ | O | —CH₂CF₃ | |
| 173 | 4-F | H | CH₃ | O | —C₂H₅ | |
| 174 | 4-F | H | CH₃ | O | —CH₂CF₃ | |
| 175 | H | H | C₃H₇—n | O | —CH₃ | oil $n_D^{24}$ 1.5913 |
| 176 | H | H | H | O | —CH₂—CH=CH₂ | |
| 177 | H | H | cyclopropyl | O | —CH₂CH₂Cl | |
| 178 | H | H | C₃H₇—n | O | —CH₂CH₂OH | |
| 179 | 4-OCHF₂ | H | CH₃ | O | —CH(CH₃)CH₃ | |
| 180 | 4-F | H | CH₃ | O | —CH₂C≡CH | |
| 181 | H | H | C₃H₇—n | O | —C₂H₅ | |
| 182 | H | H | H | O | —C₂H₅ | |
| 183 | 4-OC₂H₅ | H | CH₃ | O | —CH₃ | |
| 184 | H | H | H | O | —C(CH₃)₃ | |
| 185 | H | H | C₃H₇—n | O | —CH₂—CH=CH₂ | |
| 186 | H | H | cyclopropyl | O | —CH₂CF₃ | |
| 187 | 2-Cl | H | CH₃ | O | —CH₃ | |
| 188 | H | H | C₃H₇—n | O | —CH₂CH₂OC₂H₅ | |
| 189 | 4-OC₂H₅ | H | CH₃ | O | —C₂H₅ | |
| 190 | H | H | C₃H₇—n | O | —CH₂—C(CH₃)=CH₂ | |
| 191 | 4-OC₂H₅ | H | CH₃ | O | —CH₂CF₃ | |
| 192 | 2-Cl | H | CH₃ | O | —C₂H₅ | |
| 193 | H | H | cyclopropyl | O | —CH₂—C≡CH | |
| 194 | 4-OC₂H₅ | H | CH₃ | O | —CH₂OCH₂CH₂OCH₃ | $n_D^{24}$: 1.6128 |
| 195 | H | H | H | O | —CH₃ | |
| 196 | H | H | C₃H₇—n | O | —CH₂CH₂OCH₃ | |
| 197 | 2-Cl | H | CH₃ | O | —CH₂CF₃ | |
| 198 | H | H | CF₃ | O | —CH₃ | m.p. 63–65° C. |
| 199 | 2-F | H | CH₃ | O | —CH₃ | |
| 200 | 3-F | 4-CH₃ | CH₃ | O | —CH₃ | |
| 201 | 4-OCF₂CHF₂ | H | CH₃ | O | —CH₃ | |
| 202 | 2-Cl | 4-Cl | CH₃ | O | —CH₃ | |
| 203 | H | H | H₃C-cyclopropyl | O | —CH₃ | m.p. 51–53° C. |
| 204 | 2-OCH₃ | 5-CH₃ | CH₃ | O | —CH₃ | |
| 205 | 3-F | H | CH₃ | O | —CH₃ | m.p. 50–51° C. |
| 206 | 2-F | 4-F | CH₃ | O | —CH₃ | |
| 207 | 2-CF₃ | H | CH₃ | O | —CH₃ | m.p. 101–103° C. |
| 208 | 2-Br | 4-CH₃ | CH₃ | O | —CH₃ | |
| 209 | 4-OCF₂CHClF | H | CH₃ | O | —CH₃ | |

TABLE-continued

Compounds of the formula

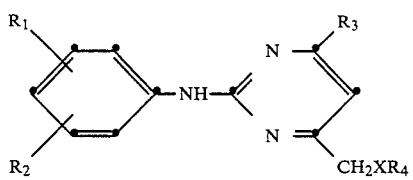

| Comp. No. | R₁ | R₂ | R₃ | X | R₄ | Physical data |
|---|---|---|---|---|---|---|
| 210 | H | H | (cyclopropyl-Cl) | O | —CH₃ | m.p. 76–78° C. |
| 211 | 3-Cl | 4-OCH₃ | CH₃ | O | —CH₃ | |
| 212 | 3-OC₂H₅ | H | CH₃ | O | —CH₃ | |
| 213 | H | H | (cyclopropyl-F) | O | —CH₃ | |
| 214 | 4-OCF₃ | H | CH₃ | O | —CH₃ | |
| 215 | 2-C₃H₇—i | H | CH₃ | O | —CH₃ | |
| 216 | H | H | —CF₂Cl | O | —CH₃ | m.p. 59–60° C. |
| 217 | H | H | CH₃ | O | —CH₃ | |
| 218 | 4-C₃H₇—i | H | CH₃ | O | —CH₃ | |
| 219 | 2-Cl | 6-CH₃ | CH₃ | O | —CH₃ | |
| 220 | H | H | —CF₂CF₃ | O | —CH₃ | m.p. 63–65° C. |
| 221 | 4-OCF₂CHCl₂ | H | CH₃ | O | —CH₃ | |
| 222 | 3-Cl | 4-CH₃ | CH₃ | O | —CH₃ | |
| 223 | 2-OCH₃ | H | CH₃ | O | —CH₃ | |
| 224 | 2-Cl | 4-CH₃ | CH₃ | O | —C₂H₅ | |
| 225 | 2-CH₃ | 3-Cl | CH₃ | O | —CH₃ | |
| 226 | H | H | —CH(CH₃)C₂H₅ | O | —CH₃ | oil $n_D^{24}$: 1.5791 |
| 227 | 2-Cl | 5-CH₃ | CH₃ | O | —CH₃ | |
| 228 | H | H | (cyclopropyl-H₃C, Cl, Cl) | O | —CH₃ | |
| 229 | 3-OCH₃ | H | CH₃ | O | —CH₃ | |
| 230 | 3-C₂H₅ | H | CH₃ | O | —CH₃ | |
| 231 | H | H | (cyclopropyl-CH₃) | O | —CH₃ | oil $n_D^{24}$: 1.6169 |
| 232 | 3-F | 5-F | CH₃ | O | —CH₃ | |
| 233 | 4-OC₃H₇—i | H | CH₃ | O | —CH₃ | |
| 234 | 2-CH₃ | 5-F | CH₃ | O | —CH₃ | |
| 235 | 4-C₂H₅ | H | CH₃ | O | —CH₃ | |
| 236 | 2-Cl | 4-OCHF₂ | CH₃ | O | —CH₃ | m.p. 65–67° C. |
| 237 | 2-CH₃ | 4-OCH₃ | CH₃ | O | —CH₃ | |
| 238 | 2-CF₃ | H | CH₃ | O | —C₂H₅ | |
| 239 | 2-C₂H₅ | H | CH₃ | O | —CH₃ | |
| 240 | 2-Cl | 4-Br | CH₃ | O | —CH₃ | |
| 241 | 2-OCHF₂ | H | CH₃ | O | —CH₃ | |
| 242 | 3-CF₃ | 5-CF₃ | CH₃ | O | —CH₃ | |
| 243 | 2-CH₃ | 4-OCHF₂ | CH₃ | O | —CH₃ | oil $n_D^{24}$: 1.5493 |
| 244 | 2-OCH₃ | 5-Cl | CH₃ | O | —CH₃ | |
| 245 | 2-CF₃ | 4-Cl | CH₃ | O | —CH₃ | |
| 246 | 3-Cl | 4-F | CH₃ | O | —CH₃ | |
| 247 | 2-CH₃ | 4-Br | CH₃ | O | —CH₃ | |
| 248 | 4-CF₃ | H | CH₃ | O | —CH₃ | m.p. 75–78° C. |
| 249 | 3-CH₃ | 4-Br | CH₃ | O | —CH₃ | |

TABLE-continued

Compounds of the formula

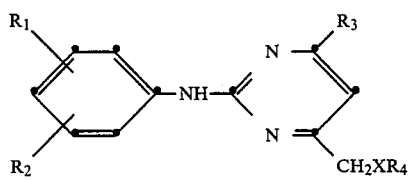

| Comp. No. | $R_1$ | $R_2$ | $R_3$ | X | $R_4$ | Physical data |
|---|---|---|---|---|---|---|
| 250 | 3-$CF_3$ | H | $CH_3$ | O | —$CH_3$ | m.p. 101–103° C. |
| 251 | H | H | —$CH_2OH$ | O | —$CH_3$ | oil $n_D^{24}$: 1.6236 |
| 252 | 3-$CH_3$ | H | $CH_3$ | O | —$CH_3$ | oil $n_D^{24}$: 1.5902 |
| 253 | 2-Cl | 5-$CF_3$ | $CH_3$ | O | —$CH_3$ | |
| 254 | 2-$CH_3$ | 6-$CH_3$ | $CH_3$ | O | —$CH_3$ | |
| 255 | 2-$CH_3$ | 4-Cl | $CH_3$ | O | —$CH_3$ | |
| 256 | H | H | —$CH_2Cl$ | O | —$CH_3$ | oil $n_D^{24}$: 1.6188 |
| 257 | 2-F | 3-F | $CH_3$ | O | —$CH_3$ | |
| 258 | 4-J | H | $CH_3$ | O | —$CH_3$ | |
| 259 | H | H | —$CHCl_2$ | O | —$CH_3$ | |
| 260 | 3-$CH_3$ | 5-$CH_3$ | $CH_3$ | O | —$CH_3$ | |
| 261 | 2-$CH_3$ | 5-Cl | $CH_3$ | O | —$CH_3$ | |
| 262 | H | H | —$CH_2F$ | O | —$CH_3$ | oil $n_D^{24}$: 1.6173 |
| 263 | 2-$CH_3$ | 3-F | $CH_3$ | O | —$CH_3$ | |
| 264 | H | H | —$CH_2OH$ | O | —$C_2H_5$ | |
| 265 | 2-$CH_3$ | H | $CH_3$ | O | —$CH_3$ | |
| 266 | 2-Br | 4-Br | $CH_3$ | O | —$CH_3$ | |
| 267 | H | H | Br-cyclopropyl | O | —$CH_3$ | |
| 268 | H | H | —$CH_2Br$ | O | —$CH_3$ | oil $n_D^{25}$: 1.6204 |
| 269 | H | H | —$CCl_3$ | O | —$CH_3$ | |
| 270 | 3-Br | H | $CH_3$ | O | —$CH_3$ | |
| 271 | 2-Br | 5-Br | $CH_3$ | O | —$CH_3$ | |
| 272 | H | H | F,$CH_3$-cyclopropyl | O | —$CH_3$ | |
| 273 | H | H | $CH_3$ | O | cyclopropyl | |
| 274 | H | H | —$CH_2Cl$ | O | —$C_2H_5$ | |
| 275 | 2-Cl | 3-Cl | $CH_3$ | O | —$CH_3$ | |
| 276 | H | H | F-cyclopropyl | O | —$CH_3$ | oil $n_D^{24}$: 1.6098 |
| 277 | H | H | $H_3C$,Cl-cyclopropyl | O | —$CH_3$ | |
| 278 | 2-Br | H | $CH_3$ | O | —$CH_3$ | |
| 279 | H | H | Cl-cyclopropyl | O | —$CH_3$ | |
| 280 | 2-$CH_3$ | 3-$CH_3$ | $CH_3$ | O | —$CH_3$ | |
| 281 | H | H | $CH_3$ | O | cyclobutyl | |
| 282 | H | H | —$CH_2F$ | O | —$C_2H_5$ | |
| 283 | 2-Cl | 5-Cl | $CH_3$ | O | —$CH_3$ | |
| 284 | 2-$OCH_3$ | 4-$OCH_3$ | $CH_3$ | O | —$CH_3$ | |

TABLE-continued

Compounds of the formula

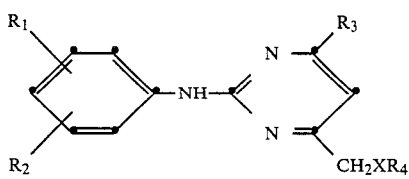

| Comp. No. | R$_1$ | R$_2$ | R$_3$ | X | R$_4$ | Physical data |
|---|---|---|---|---|---|---|
| 285 | H | H | cyclopropyl-Br | O | —CH$_3$ | |
| 286 | 2-Cl | 6-Cl | CH$_3$ | O | —CH$_3$ | |
| 287 | H | H | cyclopropyl(Br)(Cl)(Cl) | O | —CH$_3$ | |
| 288 | 2-CH$_3$ | 4-CH$_3$ | CH$_3$ | O | —CH$_3$ | |
| 289 | H | H | cyclopropyl(Cl)(CH$_3$)(CH$_3$) | O | —CH$_3$ | |
| 290 | 3-CH$_3$ | 4-CH$_3$ | CH$_3$ | O | —CH$_3$ | |
| 291 | H | H | —CH$_2$Br | O | —C$_2$H$_5$ | |
| 292 | 2-F | 5-F | CH$_3$ | O | —CH$_3$ | |
| 293 | H | H | cyclopropyl(CH$_3$)(CH$_3$) | O | —CH$_3$ | |
| 294 | 2-CH$_3$ | 5-CH$_3$ | CH$_3$ | O | —CH$_3$ | |
| 295 | 3-OCH$_3$ | 4-CH$_3$ | CH$_3$ | O | —CH$_3$ | |
| 296 | 3-F | 4-F | CH$_3$ | O | —CH$_3$ | |
| 297 | 2-F | 6-F | CH$_3$ | O | —CH$_3$ | |
| 298 | H | H | cyclopropyl(F)(F) | O | —CH$_3$ | |
| 299 | H | H | cyclopropyl(Br)(CH$_3$) | O | —CH$_3$ | |
| 300 | 3-CF$_3$ | H | CH$_3$ | O | —C$_2$H$_5$ | |
| 301 | H | H | cyclopropyl(Cl)(Cl) | O | —CH$_3$ | |
| 302 | 4-CF$_3$ | H | CH$_3$ | O | cyclopropyl | |

TABLE-continued

Compounds of the formula

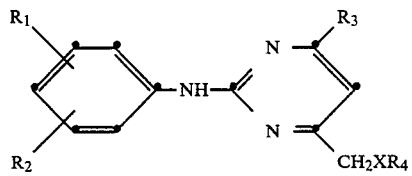

| Comp. No. | $R_1$ | $R_2$ | $R_3$ | X | $R_4$ | Physical data |
|---|---|---|---|---|---|---|
| 303 | H | H | ![](CH3/CH3 cyclopropyl) | O | —$CH_3$ | |
| 304 | 4-$OCF_3$ | H | $CH_3$ | O | —$C_2H_5$ | |
| 305 | H | H | ![](H3C/Br cyclopropyl) | O | —$CH_3$ | |
| 306 | 2-F | H | $CH_3$ | O | —$C_2H_5$ | |
| 307 | 4-$CF_3$ | H | $CH_3$ | O | —$C_2H_5$ | |
| 308 | H | H | ![](Br/Br cyclopropyl) | O | —$CH_3$ | |
| 309 | 2-Br | 6-Br | $CH_3$ | O | —$CH_3$ | |
| 310 | H | H | ![](H3C/Br/CH3 cyclopropyl) | O | —$CH_3$ | |
| 311 | H | H | ![](H3C/CH3/CH3 cyclopropyl) | O | —$CH_3$ | |
| 312 | 2-$OCH_3$ | 5-$OCH_3$ | $CH_3$ | O | —$CH_3$ | |
| 313 | H | H | ![](Cl/Cl/Cl cyclopropyl) | O | —$CH_3$ | |
| 314 | 3-$OCH_3$ | 5-$OCH_3$ | $CH_3$ | O | —$CH_3$ | |
| 315 | H | H | ![](Br/CH3 cyclopropyl) | O | —$CH_3$ | |
| 316 | 2-$CF_3$ | H | $CH_3$ | O | | |

TABLE-continued

Compounds of the formula

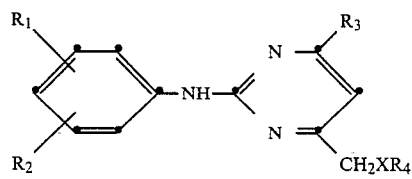

| Comp. No. | $R_1$ | $R_2$ | $R_3$ | X | $R_4$ | Physical data |
|---|---|---|---|---|---|---|
| 317 | H | H | ![Br cyclopropyl CH3] | $CH_3$ O | $-CH_3$ | |

2. FORMULATION EXAMPLES FOR LIQUID ACTIVE INGREDIENTS OF FORMULA I
(throughout, percentages are by weight)

| 2.1. Emulsifiable concentrates | (a) | (b) | (c) |
|---|---|---|---|
| a compound of the Table | 25% | 40% | 50% |
| calcium dodecylbenzenesulphonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any desired concentration can be produced from such concentrates by dilution with water.

| 2.2. Solutions | (a) | (b) | (c) | (d) |
|---|---|---|---|---|
| a compound of the Table | 80% | 10% | 5% | 95% |
| ethylene glycol monomethyl ether | 20% | — | — | — |
| polyethylene glycol (mol. wt. 400) | — | 70% | — | — |
| N—methyl-2-pyrrolidone | — | 20% | — | — |
| epoxidised coconut oil | — | — | 1% | 5% |
| ligroin (boiling range 160–190° C.) | — | — | 94% | — |

These solutions are suitable for application in the form of micro-drops.

| 2.3. Granulates | (a) | (b) |
|---|---|---|
| a compound of the Table | 5% | 10% |
| kaolin | 94% | — |
| highly dispersed silicic acid 1% - attapulgite | — | 90% |

The active ingredient is dissolved in methylene chloride, the solution is sprayed onto the carrier, and the solvent is subsequently evaporated off in vacuo.

| 2.4. Dusts | (a) | (b) |
|---|---|---|
| a compound of the Table | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

FORMULATION EXAMPLES FOR SOLID ACTIVE INGREDIENTS OF FORMULA I
(throughout, percentages are by weight)

| 2.5. Wettable powders | (a) | (b) | (c) |
|---|---|---|---|
| a compound of the Table | 25% | 50% | 75% |
| sodium lignosulphonate | 5% | 5% | — |
| sodium laurylsulphate | 3% | — | 5% |
| sodium diisobutylnaphthalene-sulphonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 2.6. Emulsifiable concentrate | |
|---|---|
| a compound of the Table | 10% |
| octylphenol polyethylene glycol ether (4–5 moles of ethylene oxide) | 3% |
| calcium dodecylbenzenesulphonate | 3% |
| castor oil polyglycol ether (35 moles of ethylene oxide) | 4% |
| cyclohexanone | 30% |
| xylene mixture | 50% |

Emulsions of any required concentration can be obtained from this concentrate by dilution with water.

| 2.7. Dusts | (a) | (b) |
|---|---|---|
| a compound of the Table | 5% | 8% |
| talcum | 95% | — |
| kaolin | — | 92% |

Ready-for-use dusts are obtained by mixing the active ingredient with the carrier and grinding the mixture in a suitable mill.

| 2.8. Extruder granulate | |
|---|---|
| a compound of the Table | 10% |
| sodium lignosulphonate | 2% |
| carboxymethylcellulose | 1% |

-continued

| 2.8. Extruder granulate | |
|---|---|
| kaolin | 87% |

The active ingredient is mixed and ground with the adjuvants, and the mixture is subsequently moistened with water. The mixture is extruded and then dried in a stream of air.

| 2.9. Coated granulate | |
|---|---|
| a compound of the Table | 3% |
| polyethylene glycol (mol. wt. 200) | 3% |
| kaolin | 94% |

The finely ground active ingredients is uniformly applied, in a mixer, to the kaolin moistened with polyethylene glycol. Non-dusty coated granulates are obtained in this manner.

| 2.10. Suspension concentrate | |
|---|---|
| a compound of the Table | 40% |
| ethylene glycol | 10% |
| nonylphenol polyethylene glycol ether (15 moles of ethylene oxide) | 6% |
| sodium lignosulphonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

3. BIOLOGICAL EXAMPLES

Example 3.1: Action Against *Puccinia graminis* On Wheat (a) Residual protective action Wheat plants are treated 6 days after sowing with a spray mixture (0.02% active ingredient) prepared from a wettable powder formulation of the test compound. After 24 hours the treated plants are infected with a uredospore suspension of the fungus. The infected plants are incubated for 48 hours at 95–100% relative humidity and about 20° C. and then stood in a greenhouse at about 22° C. Evaluation of rust pustule development is made 12 days after infection.

(b) Systemic action

Wheat plants are treated 5 days after sowing with a spray mixture (0.006% active ingredient, based on the volume of the soil) prepared from a wettable powder formulation of the test compound. After 48 hours the treated plants are infected with a uredospore suspension of the fungus. The infected plants are then incubated for 48 hours at 95–100% relative humidity and about 20° C. and then stood in a greenhouse at about 22° C. Evaluation of rust pustule development is made 12 days after infection.

Compounds of the Table exhibit good activity against Puccinia fungi (less than 20% attack). On the other hand, Puccinia attack is 100% on untreated and infected control plants.

EXAMPLE 3.2: Action Against Phytophthora On Tomato Plants (a) Residual protective action After a cultivation period of three weeks, tomato plants are sprayed with a spray mixture (0.02% active ingredient) prepared from a wettable powder formulation of the test compound. After 24 hours the treated plants are infected with a sporangia suspension of the fungus. Evaluation of fungus attack is made after incubation of the infected plants for 5 days at 90–100% relative humidity and 20° C.

(b) Residual curative action

After a cultivation period of three weeks, tomato plants are infected with a sporangia suspension of the fungus. The infected plants are then incubated for 22 hours in a humidity chamber at 90–100% relative humidity and 20° C. and are then dried and sprayed with a spray mixture (0.02% active ingredient) prepared from a wettable powder formulation of the test compound. After the spray coating has dried, the treated plants are again placed in the humidity chamber. Evaluation of fungus attack is made 5 days after infection.

(c) Systemic action

After a cultivation period of three weeks, a spray mixture (0.002% active ingredient, based on the volume of the soil) prepared from a wettable powder formulation of the test compound is poured onto tomato plants. Care is taken that the spray mixture does not come into contact with the parts of the plants above the soil. The treated plants are infected 48 hours later with a sporangia suspension of the fungus. Evaluation of fungus attack is made after incubation of the infected plants for 5 days at 90–100% relative humidity and 20° C.

Compounds of the Table exhibit good activity against Phytophthora (less than 20% attack). On the other hand, Phytophthora attack is 100% on untreated and infected control plants.

Example 3.3: Action Against Plasmopara Viticola On Vines

Residual protective action

Vine seedlings in the 4–5 leaf stage are sprayed with a spray mixture (0.02% active ingredient) prepared from a wettable powder formulation of the test compound. After 24 hours the treated plants are infected with a sporangia suspension of the fungus. Fungus attack is evaluated after incubation for 6 days at 95–100% relative humidity and 20° C.

compounds of Table exhibit good activity against Plasmopara. On the other hand, Plasmopara attack is 100% on untreated and infected control plants.

Example 3.4: Action Against *Cercospora arachidicola* On Groundnut Plants

Residual protective action

Groundnut plants 10–15 cm in height are sprayed with a spray mixture (0.02% active ingredient) prepared from a wettable powder formulation of the test compound, and infected 48 hours later with a conidia suspension of the fungus. The infected plants are incubated for 72 hours at about 21° C. and high humidity and then stood in a greenhouse until the typical leaf specks appear. Evaluation of the fungicidal action is made 12 days after infection and is based on the number and size of the specks.

Compounds of the Table exhibit good activity against Cercospora (less than 20% attack). On the other hand, Cercospora attack is 100% on untreated and infected control plants.

Example 3.5: Action Against *Venturia inaequalis* On Apple Shoots

Residual protective action

Apple cuttings with 10–20 cm long fresh shoots are sprayed with a spray mixture (0.02% active ingredient) prepared from a wettable powder formulation of the test compound. The treated plants are infected 24 hours later with conidia suspension of the fungus. The plants are then incubated for 5 days at 90–100% relative humidity and stood in a greenhouse for a further 10 days at 20°–24° C. Scab infestation is evaluated 15 days after infection.

Compounds of the Table exhibit good activity against Venturia; thus e.g. compound nos. 1, 10, 38, 59, 231, 262 and 276 reduce Venturia attack to less than 10%. On the other hand, Venturia attack is 100% in untreated and infected control plants.

Example 3.6 Action against Botrytis Cinerea on apple fruits

Residual protective action

Artificially damaged apples are treated by the dropwise application to the damaged sites of a spray mixture (0.002% active ingredient) prepared from a wettable powder formulation of the test compound. The treated fruits are then inoculated with a spore suspension of the fungus and incubated for one week at high humidity and about 20° C. Evaluation is made by counting the rotted damaged sites and deriving the fungicidal activity of the test compound therefrom.

Compounds of the Table exhibit good activity against Botrytis (less than 20% attack). Thus e.g. compounds nos. 1, 3, 7, 10, 38, 59, 231, 256, 262, 268 and 276 reduce Botrytis attack to 0 to 5%. On the other hand, Botrytis attack is 100% on untreated and infected control plants.

Example 3.7: Action Against *Erysiphe graminis* On Barley

Residual protective action

Barley plants about 8 cm in height are sprayed with a spray mixture (0.02% active ingredient) prepared from a wettable powder formulation of the test compound. The treated plants are dusted with conidia of the fungus after 3 to 4 hours. The infected barley plants are stood in a greenhouse at about 22° C. The fungus attack is evaluated after 10 days.

Compounds of the Table exhibit good activity against Erysiphe; Thus e.g. compounds nos. 1, 5, 6, 10, 38, 59, 135, 175, 231 and 262 reduce Erysiphe attack to less than 20%. On the other hand, Erysiphe attack is 100% on untreated and infected control plants.

Example 3.8: Action Against *Helminthosporium gramineum*

Wheat grains are contaminated with a spore suspension of the fungus and dried. The contaminated grains are dressed with a suspension of the test compound prepared from a wettable powder (600 ppm of active ingredient, based on the weight of the seeds). Two days later the grains are placed in suitable agar dishes and the development of fungus colonies around the grains is assessed after another 4 days. The effectiveness of test compounds is evaluated on the basis of the number and size of the colonies. The compounds of the table substantially prevent fungus attack (0 to 10%).

Example 3.9: Action Against *Fusarium nivale*

Wheat grains are contaminated with a spore suspension of the fungus and dried. The contaminated grains are dresses with a suspension of the test compound prepared from a wettable powder (600 ppm of active ingredient, based on the weight of the seeds). Two days later the grains are placed is suitable agar dished and the development of fungus colonies around the grains is assessed after another 4 days. The effectiveness of the test compounds is evaluated on the basis of the number and size of the colonies.

In the case of grains treated with a wettable powder containing as active ingredient a compound of the Table, the development of the fungus colonies was inhibited almost completely (0 to 5%).

Example 3.10: Action against *Tilletia caries*

Barley grains are contaminated with a spore suspension of the fungus and dried. The contaminated grains are dressed with a suspension of the test compound prepared from a wettable powder (600 ppm of active ingredient, based on the weight of the seeds). Two days later the grains are placed in suitable agar dished and the development of fungus colonies around the grains is assessed after another 4 days. The effectiveness of the test compounds is evaluated on the basis of the number and size of the colonies. The compounds of the Table substantially inhibit fungus attack (0 to 10%).

Example 3.11; Action Against *Colletotrichum lagenarium* On Cucumbers (*Cucumis sativus L.*)

After a cultivation period of two weeks, cucumber plants are sprayed with a spray mixture (concentration 0.02%) prepared from a wettable powder formulation of the test compound. After two days the plants are infected with a spore suspension ($1.5 \times 10^5$ spores/ml) of the fungus and incubated for 36 hours in the dark at 23° C. and high humidity. Incubation is then continued at normal humidity and about 22°–23° C. Evaluation of fungus attack is made 8 days after infection. Fungus attack is 100% on untreated and infected control plants.

Compounds of the Table exhibit good activity and inhibit the spread of the disease. Fungus attack is reduced to 20% or less.

Example 3.12: Action Against *Septoria nodorum* On Wheat

Residual protective action 7-day-old wheat plants are sprayed with a spray mixture (concentration 0.02%) prepared from the formulated test compound and two days later are infected with conidia suspension (400,000 conidia/ml, with the addition of 0.1% Tween 20 as wetting agent) of Septoria nodorum. After an incubation phase of two days in a greenhouse compartment at 20° C. and 95–100% relative humidity, the test plants are placed uncovered in a greenhouse compartment at 21° C. and 60% relative humidity until the end of the test. Evaluation of fungus attack is made 7 to 10 days after infection.

While untreated and infected plants exhibit 100% attack, plants treated with compounds of the Table exhibit fungus attack of less than 20%.

Example 3.13: Action Against *Alternaria solani* on Tomatoes

Residual protective action 3-week-old tomato plants are sprayed with a spray mixture (concentration 0.02%) prepared from the formulated test compound and 2 days later are infected on both sides with a conidia suspension (20,00 conidia/ml) of Alternaria solani. In order to prevent the fine drops of the spray coating from being washed off, the infected plants are covered with close-meshed nets in a first incubation phase of 3 days in a greenhouse compartment at 20° C. and 100% relative humidity. The plants are then placed in a greenhouse compartment at 24° C. until the end of the test. Evaluation of fungus attack is made 4 days after infection.

While untreated and infected control plants exhibit 100% attack, plants treated with compounds of the Table exhibit fungus attack of less than 20%.

Example 3.14

(a) Insecticidal contact action against *Nephotettix cincticeps* and *Nilaparvata lugens* (nymphs)

The test is carried out with growing rice plants. For this purpose 4 plants (14–20 days old) about 15 cm in height are planted into each of a number of pots (diameter 5.5 cm).

The plants in each pot are sprayed on a rotary table with 100 ml of an aqueous emulsion preparation containing 400 ppm of the test compound. After the spray coating has dried, each plant is populated with 20 nymphs of the test organisms in the third stage. To prevent the cicadas from escaping, a glass cylinder which is open at both ends is slipped over each of the plants and sealed with a gauze top. The nymphs are kept on the treated plants for 6 days until they have reached the adult stage. An evaluation is made on the basis of percentage mortality 6 days after population of the plants. The test is carried out at about 27° C. and 60% relative humidity. The plants are exposed to light for a period of 16 hours per day.

(b) Systemic insecticidal action against *Nilaparvata lugens* (in water)

Rice plants about 10 days old (about 10 cm high) are placed in a plastics beaker which contains 150 ml of an aqueous emulsion preparation of the test compound in a concentration of 100 ppm and is closed by a perforated plastics lid. The roots of each of the rice plants are pushed through a hole in the plastics lid into the aqueous test preparation. Then the rice plants are populated with 20 nymphs of Nilaparvata lugens in the N2 to N3 stage and covered with a plastics cylinder. The test is carried out at about 26° C. and 60% relative humidity, and the plants are exposed to light for a period of 16 hours per day. After five days the number of dead test organisms is assessed in comparison with untreated controls. It is thus established whether the test substance absorbed via the roots kills the test organisms at the upper part of the plants.

Compounds of the Table are more than 80% effective against the mentioned rice pests both in the contact test and in the systemic test.

I claim:
1. Compounds of formula I

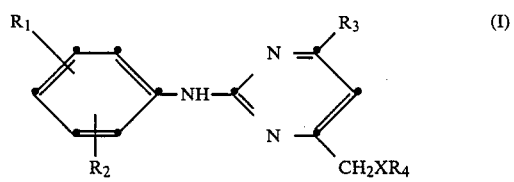

in which:
$R_1$ and $R_2$ independently of one another are hydrogen, halogen, $C_1$–$C_3$-alkyl, $C_1$–$C_2$-haloalkyl, $C_1$–$C_3$-alkoxy or $C_1$–$C_3$-haloalkoxy;
$R_3$ is hydrogen; $C_1$–$C_4$-alkyl; $C_1$–$C_2$-alkyl substituted by halogen or by hydroxy; cyclopropyl; or cyclopropyl substituted by halogen and/or by methyl;
$R_4$ is $C_1$–$C_8$-alkyl; $C_2$–$C_6$-alkyl substituted by halogen, hydroxy, cyano, $C_1$–$C_4$-alkoxy, $C_3$–$C_4$-alkoxyalkoxy or by $C_1$–$C_3$-alkylthio; $C_3$–$C_6$-alkenyl; $C_3$–$C_6$-alkynyl; $C_3$–$C_7$-cycloalkyl; or $C_3$–$C_7$-cycloalkyl substituted by methyl; and
X is oxygen or sulphur.

2. Compounds of formula I according to claim 1 in which $R_3$, $R_4$, and X have the meanings given and $R_1$ and $R_2$ are hydrogen.

3. Compounds of formula I according to claim 1 in which:
$R_1$ and $R_2$ independently of one another are hydrogen, halogen, $C_1$–$C_3$-alkyl, $C_1$–$C_2$-haloalkyl, $C_1$–$C_3$-alkoxy or $C_1$–$C_3$-haloalkoxy;
$R_3$ is hydrogen, $C_1$–$C_4$-alkyl or cyclopropyl;
$R_4$ is $C_1$–$C_8$-alkyl; $C_2$–$C_6$-alkyl substituted by halogen, hydroxy, cyano, $C_1$–$C_4$-alkoxy, $C_3$–$C_4$-alkoxyalkoxy or by $C_1$–$C_3$-alkylthio; $C_3$–$C_6$-alkenyl; $C_3$–$C_6$-alkynyl; $C_5$–$C_7$-cycloalkyl; or $C_5$–$C_7$-cycloalkyl substituted by methyl; and
X is oxygen or sulphur.

4. Compounds of formula I according to claim 3 in which:
$R_1$ and $R_2$ independently of one another are hydrogen, fluorine, chlorine, bromine, $C_1$–$C_3$-alkyl, $C_1$–$C_2$-haloalkyl, $C_1$–$C_3$-alkoxy or $C_1$–$C_2$-haloalkoxy;
$R_3$ is hydrogen, $C_1$–$C_3$-alkyl or cyclopropyl;
$R_4$ is $C_1$–$C_6$-alkyl; $C_2$–$C_4$-alkyl substituted by halogen, hydroxy, cyano, $C_1$–$C_3$-alkoxy, $C_3$–$C_4$-alkoxyalkoxy or by $C_1$–$C_2$-alkylthio; $C_3$-alkenyl; $C_3$-alkynyl; or $C_6$–$C_7$-cycloalkyl that is unsubstituted or substituted by methyl; and
X is oxygen or sulphur.

5. Compounds of formula I according to claim 3 in which:
$R_1$ and $R_2$ independently of one another are hydrogen, fluorine, chlorine, bromine, $C_1$–$C_3$-alkyl, $C_1$–$C_3$-alkoxy, trifluoromethyl, —$OCHF_2$, —$OCF_2CHF_2$, —$OCF_2CHClF$, —$OCF_2CHCl_2$ or —$OCF_2CCl_2F$;
$R_3$ is hydrogen, methyl, ethyl or n-propyl;
$R_4$ is $C_1$–$C_4$-alkyl; $C_2$–$C_3$-alkyl substituted by halogen, hydroxy, cyano, $C_1$–$C_2$-alkoxy or by $C_1$–$C_2$-alkylthio; $C_3$–$C_6$-alkenyl; $C_3$–$C_6$-alkynyl; or cyclohexyl; and
X is oxygen or sulphur.

6. Compounds of formula I according to claim 4 in which:
$R_1$ and $R_2$ independently of one another are hydrogen, fluorine, chlorine, bromine, $C_1$–$C_2$-alkyl, $C_1$–$C_2$-alkoxy, trifluoromethyl, —$OCHF_2$, —$OCF_3$, —$OCF_2CHF_2$ or —$OCF_2CHClF$;
$R_3$ is hydrogen or $C_1$–$C_2$-alkyl;

$R_4$ is $C_1$–$C_3$-alkyl; $C_2$-alkyl substituted by halogen, hydroxy, cyano, $C_1$–$C_2$-alkoxy or by $C_1$–$C_2$-alkylthio; $C_3$–$C_4$-alkenyl; or $C_3$–$C_4$-alkynyl; and X is oxygen or sulphur.

7. Compounds of formula I according to claim 6 in which:

$R_1$ and $R_2$ independently of one another are hydrogen, fluorine, chlorine, bromine, $C_1$–$C_2$-alkyl, $C_1$–$C_2$-alkoxy, trifluoromethyl or —OCHF$_2$;

$R_3$ is methyl;

$R_4$ is $C_1$–$C_2$-alkyl; $C_2$-alkyl substituted by fluorine, chlorine, bromine, cyano, $C_1$–$C_2$-alkoxy or by methylthio; allyl; or propargyl; and X is oxygen or sulphur.

8. Compounds of formula I according to claim 1 in which:

$R_1$ and $R_2$ independently of one another are hydrogen, halogen, $C_1$–$C_2$-alkyl, halomethyl, $C_1$–$C_2$-alkoxy or $C_1$–$C_2$-haloalkoxy;

$R_3$ is hydrogen; $C_1$–$C_3$-alkyl; $C_1$–$C_2$-alkyl substituted by halogen or by hydroxy; cyclopropyl; or cyclopropyl mono- to tri-substituted by the same or different substituents selected from the group consisting of halogen and methyl;

$R_4$ is $C_1$–$C_4$-alkyl; $C_2$–$C_3$-alkyl substituted by halogen, cyano, $C_1$–$C_2$-alkoxy or by $C_1$–$C_2$-alkylthio; $C_3$–$C_6$-alkenyl; $C_3$–$C_6$-alkynyl; or $C_3$–$C_7$-cycloalkyl; and X is oxygen or sulphur.

9. Compounds of formula I according to claim 8 in which:

$R_1$ and $R_2$ independently of one another are hydrogen, fluorine, chlorine, bromine, methyl, trifluoromethyl, methoxy or difluoromethoxy;

$R_3$ is hydrogen; $C_1$–$C_3$-alkyl; $C_1$–$C_2$-alkyl substituted by halogen or by hydroxy, cyclopropyl; or cyclopropyl mono- to tri-substituted by the same or different substituents selected from the group consisting of halogen and methyl;

$R_4$ is $C_1$–$C_3$-alkyl; $C_2$–$C_3$-alkyl substituted by fluorine, chlorine or by $C_1$–$C_2$-alkoxy; $C_3$–$C_6$-alkenyl; $C_3$–$C_6$-alkynyl; or $C_3$–$C_6$-cycloalkyl; and X is oxygen or sulphur.

10. Compounds of formula I according to claim 9 in which:

$R_1$ and $R_2$ independently of one another are hydrogen, fluorine, chlorine, methyl, trifluoromethyl, methoxy or difluoromethoxy;

$R_3$ is $C_1$–$C_3$-alkyl; methyl substituted by halogen or by hydroxy; cyclopropyl; or cyclopropyl mono- to tri-substituted by halogen or by methyl;

$R_4$ is $C_1$–$C_3$-alkyl; $C_2$–$C_3$-alkyl substituted by fluorine, chlorine or by methoxy; $C_3$–$C_4$-alkenyl; $C_3$–$C_4$-alkynyl; cyclopropyl; or cyclohexyl; and X is oxygen.

11. Compounds of formula I according to claim 10 in which:

$R_1$ and $R_2$ are hydrogen;

$R_3$ is $C_1$–$C_3$-alkyl; methyl substituted by fluorine, chlorine or by bromine; cyclopropyl; or cyclopropyl substituted by chlorine or by methyl;

$R_4$ is $C_1$–$C_3$-alkyl. 2-chloroethyl, 2,2,2-trifluoroethyl, allyl or propargyl; and X is oxygen.

12. A compound of formula I according to claim 3 selected from 2-phenylamino-4-methyl-6-methoxymethylpyrimidine;

2-phenylamino-4-cyclopropyl-6-methoxymethylpyrimidine.

13. A composition for controlling or preventing an attack by insect pests or phytopathogenic microorganisms which comprises as the active component a compound of claim 1.

14. A composition for controlling or preventing an attack by insect pests or phytopathogenic microorganisms which comprises as the active component a compound of claim 2.

15. A composition for controlling or preventing an attack by insect pests or phytopathogenic microorganisms which comprises as the active component a compound of claim 3.

16. A composition for controlling or preventing an attack by insect pests or phytopathogenic microorganisms which comprises as the active component a compound of claim 12.

17. A composition according to claim 13 which comprises from 0.1 to 99% by weight of a compound of formula I, from 99.9 to 1% by weight of a solid or liquid adjuvant and from 0 to 25% by weight of a surfactant.

18. A method of controlling or preventing an attack of cultivated plants by insect pests or phytopathogenic microorganisms which comprises the step of applying a compound of claim 1 to the plant or its locus.

19. A method of controlling or preventing an attack of cultivated plants by harmful phytopathogenic microorganisms which comprises the step of applying a compound of claim 1 to the plant or its locus.

20. A method according to claim 19 wherein the microorganisms are phytopathogenic fungi.

* * * * *